United States Patent
Kapadia et al.

(10) Patent No.: US 12,044,586 B2
(45) Date of Patent: Jul. 23, 2024

(54) METHOD OF CALIBRATING TORQUE SENSORS OF INSTRUMENT DRIVE UNITS OF A SURGICAL ROBOT

(71) Applicant: Covidien LP, Mansfield, MA (US)

(72) Inventors: Jaimeen Kapadia, Cambridge, MA (US); Richard Lech, Hamden, CT (US); Mark MacLeod, Brookfield, CT (US); Chi Min Seow, Watertown, MA (US); Michael Zemlok, Prospect, CT (US)

(73) Assignee: COVIDIEN LP, Mansfield, MA (US)

( * ) Notice: Subject to any disclaimer, the term of this patent is extended or adjusted under 35 U.S.C. 154(b) by 368 days.

(21) Appl. No.: 17/437,878

(22) PCT Filed: Jun. 5, 2019

(86) PCT No.: PCT/US2019/035520
§ 371 (c)(1),
(2) Date: Sep. 10, 2021

(87) PCT Pub. No.: WO2020/214192
PCT Pub. Date: Oct. 22, 2020

(65) Prior Publication Data
US 2022/0170809 A1    Jun. 2, 2022

Related U.S. Application Data (60) Provisional application No. 62/833,833, filed on Apr. 15, 2019.

(51) Int. Cl.
*G01L 25/00* (2006.01)
*A61B 34/00* (2016.01)
(Continued)

(52) U.S. Cl.
CPC ............ *G01L 25/003* (2013.01); *A61B 34/37* (2016.02); *A61B 34/77* (2016.02); *B25J 13/085* (2013.01)

(58) Field of Classification Search
CPC . A61B 34/37; A61B 34/77; A61B 2034/2059; A61B 2017/00725;
(Continued)

(56) References Cited

U.S. PATENT DOCUMENTS 3,797,305 A    3/1974    Haskell
5,272,423 A    12/1993    Kim
(Continued)

FOREIGN PATENT DOCUMENTS

CN    1988371 A    6/2007
EP    0457086 A2 *    11/1991
(Continued)

OTHER PUBLICATIONS

WO-2014206974-A1—English (Year: 2014).*
(Continued)

*Primary Examiner* — Kristina M Deherrera
*Assistant Examiner* — Fatemeh Esfandiari Nia
(74) *Attorney, Agent, or Firm* — Carter, DeLuca & Farrell LLP (57) ABSTRACT

A method of calibrating a torque sensor for a motor with a controller includes determining a gain of the torque sensor, zeroing a torque reading of the torque sensor, accelerating the motor at a known rate, and determining an inertia of the motor in response to accelerating the motor. Zeroing the torque reading occurs when the motor is in an unloaded and unactivated condition and accelerating the motor occurs when the motor is in an unloaded condition.

14 Claims, 6 Drawing Sheets

(51) Int. Cl.
*A61B 34/37* (2016.01)
*B25J 13/08* (2006.01)

(58) Field of Classification Search
CPC ............. A61B 2090/066; B25J 13/085; G05B 2219/39058; G05B 2219/45117; H02K 11/21; H02K 7/116; H02K 11/24; H02K 7/14

See application file for complete search history.

(56) References Cited

U.S. PATENT DOCUMENTS

| | | | |
|---|---|---|---|
| 5,327,790 | A | 7/1994 | Levin et al. |
| 5,533,410 | A | 7/1996 | Smith |
| 5,792,135 | A | 8/1998 | Madhani et al. |
| 6,591,200 | B1 * | 7/2003 | Cohen ................. G01P 21/02 |
| | | | 702/41 |
| 7,212,935 | B1 | 5/2007 | O'Brien et al. |
| 8,161,827 | B2 | 4/2012 | Kato |
| 8,281,670 | B2 | 10/2012 | Larkin et al. |
| 8,359,932 | B2 | 1/2013 | Eriksen et al. |
| 8,828,023 | B2 | 9/2014 | Neff et al. |
| 9,561,585 | B2 | 2/2017 | Tanaka |
| 9,987,094 | B2 | 6/2018 | Allen et al. |
| 10,213,266 | B2 | 2/2019 | Zemlok et al. |
| 2006/0267537 | A1 | 11/2006 | Baumann et al. |
| 2007/0129846 | A1 | 6/2007 | Birkenbach et al. |
| 2007/0143040 | A1 | 6/2007 | Ide |
| 2007/0164695 | A1 * | 7/2007 | Hagihara ................ B25J 9/1602 |
| | | | 318/568.11 |
| 2009/0248038 | A1 * | 10/2009 | Blumenkranz ........ A61B 34/30 |
| | | | 606/130 |
| 2009/0259412 | A1 | 10/2009 | Brogardh |
| 2010/0005907 | A1 | 1/2010 | Kato et al. |
| 2010/0094312 | A1 | 4/2010 | Ruiz Morales et al. |
| 2011/0009880 | A1 | 1/2011 | Prisco et al. |
| 2011/0314935 | A1 | 12/2011 | Krippner et al. |
| 2012/0048628 | A1 | 3/2012 | Kawanami et al. |
| 2012/0116416 | A1 | 5/2012 | Neff et al. |
| 2013/0317519 | A1 | 11/2013 | Romo et al. |
| 2014/0060223 | A1 | 3/2014 | Tanaka |
| 2017/0165834 | A1 | 6/2017 | Hares |
| 2017/0296179 | A1 | 10/2017 | Shelton, IV et al. |
| 2018/0153634 | A1 | 6/2018 | Zemlok et al. |
| 2018/0162153 | A1 | 6/2018 | Kanematsu |
| 2018/0262153 | A1 | 9/2018 | Tanabe |

FOREIGN PATENT DOCUMENTS

| | | | |
|---|---|---|---|
| JP | 1998210788 | 8/1998 | |
| KR | 1019940003005 | 4/1994 | |
| WO | WO-2014206974 A1 * | 12/2014 | ............ B25J 13/085 |
| WO | 2018217524 A2 | 11/2018 | |
| WO | 2019051005 A1 | 3/2019 | |

OTHER PUBLICATIONS

EP-0457086-A2—English (Year: 1991).*
International Search Report mailed Jan. 13, 2020 and Written Opinion completed Jan. 13, 2020 corresponding to counterpart Int'l Patent Application PCT/US2019/035520.
Chinese Office Action issued in corresponding Chinese Application No. 201980001125.7 dated Apr. 19, 2023, 15 pages.
Extended European Search Report dated Dec. 9, 2022 corresponding to counterpart Patent Application EP 19925074.7.
Perera et al.: "DC motor inertia estimation for robust bilateral control", 7th International Conference on Information and Automation for Sustainability, IEEE, Dec. 22, 2014 (Dec. 22, 2014), pp. 1-7, XP032752784, DOI: 10.1109/ICIAFS.2014.7069637 [retrieved on Mar. 26, 2015] * the whole document *.
Aghili et al.: "Adaptive Control of Manipulators Using Uncalibrated Joint-Torque Sensing", Robotics and Automation, 2005. Proceedings of the 2005 IEEE International Conference on Barcelona, Spain, Apr. 18-22, 2005, Piscataway, NJ, USA, IEEE, Apr. 18, 2005 (Apr. 18, 2005), pp. 1694-1699, XP010871963, DOI: 10.1109/ROBOT.2005.1570357 ISBN: 978-0-7803-8914-4 * p. 1694-p. 1699 *.

* cited by examiner

METHOD OF CALIBRATING TORQUE SENSORS OF INSTRUMENT DRIVE UNITS OF A SURGICAL ROBOT

CROSS-REFERENCE TO RELATED APPLICATIONS

The present application is a U.S. National Stage Application filed under 35 U.S.C. § 371(a) claiming the benefit of and priority to International Patent Application No. PCT/US2019/035520, filed Jun. 5, 2019, which claims the benefit of and priority to U.S. Provisional Patent Application Ser. No. 62/833,833, filed Apr. 15, 2019, the entire disclosures of each of which being incorporated by reference herein.

BACKGROUND

Robotic surgical systems have been used in minimally invasive medical procedures. During a medical procedure, the robotic surgical system is controlled by a surgeon interfacing with a user interface. The user interface allows the surgeon to manipulate an end effector of a surgical instrument that acts on a patient. The user interface includes an input controller or handle that is moveable by the surgeon to control the robotic surgical system.

Robotic surgical systems typically use a scaling factor to scale down the motions of the hands of a surgeon to determine the desired position of the end effector within the patient so that the surgeon can more precisely move the end effector inside the patient.

During a surgical procedure, it may be desirable to increase the precision of movements of the end effector within the patient. Movements of the end effector may be controlled by an Instrument Drive Unit (IDU) of a surgical robot. Some movements of the IDUs are controlled by motors or actuators that use torque sensors as a feedback mechanism disposed within the IDU.

During manufacturing of IDUs there may be small variations in the readings of torque sensors. The variations can be related to the torque sensors and/or the assembly of the IDU. The variations may be in a zero or offset of the torque sensor, e.g., when there is no load on the torque sensor. In addition, there can be variations in the gain of the torque sensors.

There is a need for methods for calibrating torque sensors of IDUs such that the movements of end effectors secured to the IDU can be precisely controlled.

SUMMARY

In an aspect of the present disclosure, a method of calibrating a torque sensor for a motor with a controller includes determining a gain of the torque sensor, zeroing a torque reading of the torque sensor, accelerating the motor at a known rate, and determining an inertia of the motor in response to accelerating the motor. Zeroing the torque reading occurs when the motor is in an unloaded and unactivated condition and accelerating the motor occurs when the motor is in an unloaded condition.

In aspects, determining the gain of the torque sensor includes interrogating a memory chip of the torque sensor itself. Accelerating the motor at the known rate may include measuring a position of the motor with a position sensor.

In some aspects, the method includes activating another motor with the motor in the unactivated condition and determining a cross talk torque of the torque sensor in response to activating the other motor.

In another aspect of the present disclosure, a method of calibrating torque sensors of an IDU with a controller with each toque sensor associated with a respective motor of the IDU includes determining a gain of each of the torque sensors, zeroing a torque reading of each of the torque sensors when each of the motors is in an unloaded and unactivated condition, and determining an inertia of each of the motors. Determining the inertia of each of the motors includes accelerating a respective motor at a known rate in an unloaded condition with each of the other motors in an unloaded and unactivated condition, measuring a torque of the respective motor with a toque sensor associated with the respective motor, and determining the inertia of the respective motor from the measured torque and the known rate of acceleration.

In aspects, determining the inertia of each of the motors includes determining a cross talk torque of each torque sensor not associated with the respective motor by measuring a torque in response to accelerating the respective motor. The method may include creating a cross talk matrix includes a correction factor for each of the torque sensors for each of the motors of the IDU.

In some aspects, determining the gain of each of the torque sensors includes interrogating a memory chip of each of the torque sensors. Accelerating the respective motor at the known rate may include measuring a position of the respective motor with a position sensor associated with the respective motor.

In another aspect of the present disclosure, a method of calibrating torque sensors of an IDU with a controller is disclosed. The IDU includes a first torque sensor that is associated with a first motor, a second torque sensor that is associated with a second motor, a third torque sensor that is associated with a third motor, and a fourth torque sensor that is associated with a fourth motor. The method includes determining a gain of each of the first, second, third, and fourth torque sensors, zeroing a torque reading of each of the first, second, third, and fourth torque sensors when each of the first, second, third, and fourth torque motors is in an unloaded and unactivated condition, and determining an inertia of the first motor. Determining the inertia of the first motor includes accelerating the first motor at a first known rate in an unloaded condition with each of the second, third, and fourth motors in an unloaded and unactivated condition, measuring a toque of the first motor with the first torque sensor, and determining the inertia of the first motor from the torque measured by the first torque sensor and the first known rate of acceleration.

In aspects, the method includes determining an inertia of the second motor, determining an inertia of the third motor, and determining an inertia of the fourth motor. Determining the inertia of the second motor includes accelerating the second motor at a second known rate in an unloaded condition with each of the first, third, and fourth motors in an unloaded and unactivated condition, measuring a torque of the second motor with the second torque sensor, and determining the inertia of the second motor from the torque measured by the second torque sensor and the second known rate of acceleration. Determining an inertia of the third motor includes accelerating the third motor at a third known rate in an unloaded condition with each of the first, second, and fourth motors in an unloaded and unactivated condition, measuring a torque of the third motor with the third torque sensor, and determining the inertia of the third motor from the torque measured by the third torque sensor and the third known rate of acceleration. Determining the inertia of the fourth motor includes accelerating the fourth motor at a fourth known rate in an unloaded condition with each of the first, second, and third motors in an unloaded and unactivated condition, measuring a torque of the fourth motor with the fourth torque sensor, and determining the inertia of the fourth motor from the torque measured by the fourth torque sensor and the fourth known rate of acceleration.

In some aspects, determining the inertia of the first motor includes determining a cross talk torque of the second, third, and fourth torque sensors in response to accelerating the first motor. Determining the inertia of the second motor may include determining a cross talk torque of the first, third, and fourth torque sensors in response to accelerating the second motor. Determining the inertia of the third motor may include determining a cross talk torque of the first, second, and fourth torque sensors in response to accelerating the third motor. Determining the inertia of the fourth motor may include determining a cross talk torque of the first, second, and third torque sensors in response to accelerating the fourth motor.

In certain aspects, the method includes creating a cross talk matrix which includes a correction factor for each of the first, second, third, and fourth torque sensors for torque from each of the first, second, third, and fourth motors. The method may include utilizing the cross talk matrix during a surgical procedure to correct torque of at least one of the first, second, third, or fourth motors.

In particular aspects, determining the inertia of the first motor includes determining a cross talk toque of the second, third, and fourth torque sensors in response to accelerating the first motor. Determining the gain of the first, second, third, and fourth torque sensors may include interrogating a memory chip of reach of the first, second, third, and fourth torque sensors. Accelerating the first motor at the known rate may include measuring a position of the first motor with a position sensor associated with the first motor.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closer to the clinician or surgical robot and the term "distal" refers to the portion of the device or component thereof that is farther from the clinician or surgical robot. In addition, as used herein the term "pose" is understood to mean a position and orientation of an object in space. Further, as used herein the term "neutral" is understood to mean non-scaled.

This disclosure generally relates to a method of calibrating torque transducers of an instrument drive unit (IDU) of a surgical robot. The method includes accounting for differences in gain of each torque sensor of the IDU, accounting for the temperature effects of each torque sensor of the IDU, zeroing each torque sensor, determining the inertia of each motor of the IDU, and accounting for the cross-talk of each motor with each of the torque sensors of the IDU. By calibrating torque transducers of the IDU before a surgical procedure, movements of tools attached to the IDU may be more accurately controlled during a surgical procedure which may result in improved surgical outcomes for patients and/or reduce the time and/or costs of a surgical procedure.

Figure 1:
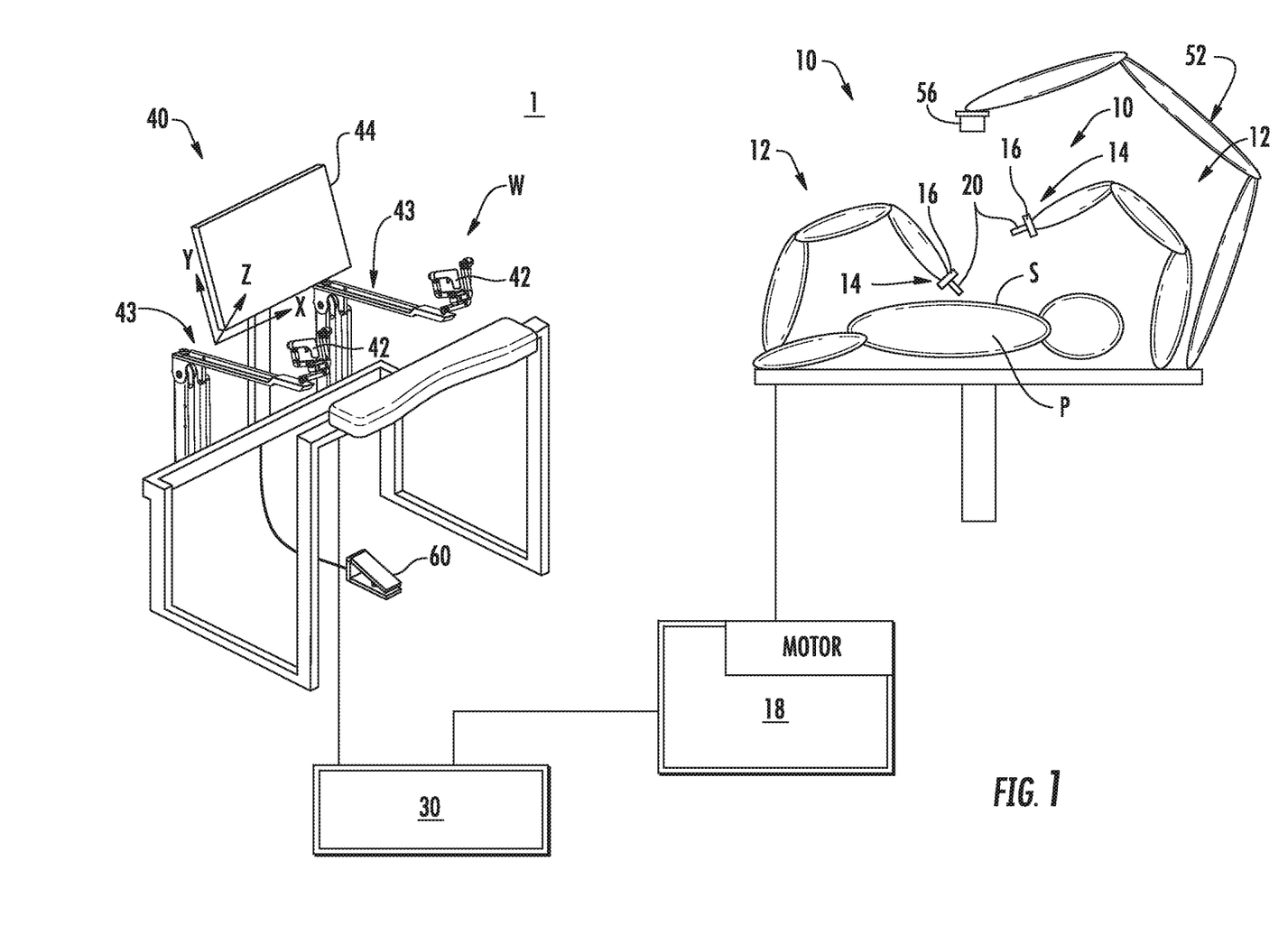
FIG. 1 is a is a schematic illustration of a user console and a surgical robot of a robotic surgical system in accordance with the present disclosure.

Referring to FIG. 1, a robotic surgical system 1 in accordance with the present disclosure is shown generally as a surgical robot 10, a processing unit 30, and a user console 40. The surgical robot 10 generally includes linkages 12 and a robot base 18. The linkages 12 moveably support an end effector or tool 20 which is configured to act on tissue. The linkages 12 may be in the form of arms each having an end 14 that supports the end effector or tool 20 which is configured to act on tissue. In addition, the ends 14 of the linkages 12 may include an imaging device 16 for imaging a surgical site "S". The user console 40 is in communication with robot base 18 through the processing unit 30.

The user console 40 includes a display device 44 which is configured to display three-dimensional images. The display device 44 displays three-dimensional images of the surgical site "S" which may include data captured by imaging devices 16 positioned on the ends 14 of the linkages 12 and/or include data captured by imaging devices that are positioned about the surgical theater (e.g., an imaging device positioned within the surgical site "S", an imaging device positioned adjacent the patient "P", imaging device 56 positioned at a distal end of an imaging arm 52). The imaging devices (e.g., imaging devices 16, 56) may capture visual images, infra-red images, ultrasound images, X-ray images, thermal images, and/or any other known real-time images of the surgical site "S". The imaging devices transmit captured imaging data to the processing unit 30 which creates three-dimensional images of the surgical site "S" in real-time from the imaging data and transmits the three-dimensional images to the display device 44 for display.

The user console 40 also includes input handles 42 which are supported on control arms 43 which allow a clinician to manipulate the surgical robot 10 (e.g., move the linkages 12, the ends 14 of the linkages 12, and/or the tools 20). Each of the input handles 42 is in communication with the processing unit 30 to transmit control signals thereto and to receive feedback signals therefrom. Additionally or alternatively, each of the input handles 42 may include input devices (not explicitly shown) which allow the surgeon to manipulate (e.g., clamp, grasp, fire, open, close, rotate, thrust, slice, etc.) the tools 20 supported at the ends 14 of the linkages 12.

Each of the input handles 42 is moveable through a predefined workspace to move the ends 14 of the linkages 12, e.g., tools 20, within a surgical site "S". The three-dimensional images on the display device 44 are orientated such that the movement of the input handles 42 moves the ends 14 of the linkages 12 as viewed on the display device 44. The three-dimensional images remain stationary while movement of the input handles 42 is scaled to movement of the ends 14 of the linkages 12 within the three-dimensional images. To maintain an orientation of the three-dimensional images, kinematic mapping of the input handles 42 is based on a camera orientation relative to an orientation of the ends 14 of the linkages 12. The orientation of the three-dimensional images on the display device 44 may be mirrored or rotated relative to the view captured by the imaging devices 16, 56. In addition, the size of the three-dimensional images on the display device 44 may be scaled to be larger or smaller than the actual structures of the surgical site permitting a clinician to have a better view of structures within the surgical site "S". As the input handles 42 are moved, the tools 20 are moved within the surgical site "S" as detailed below. Movement of the tools 20 may also include movement of the ends 14 of the linkages 12 which support the tools 20.

For a detailed discussion of the construction and operation of a robotic surgical system 1, reference may be made to U.S. Pat. No. 8,828,023, the entire contents of which are incorporated herein by reference.

The user console 40 further includes a foot pedal 60 that can be used to control various aspects of the robotic surgical system 1. For example, the foot pedal 60 may be selectively associated with an input handle, e.g., input handle 42, to actuate a tool 20 associated with the respective input handle. Additionally or alternatively, the foot pedal 60 may be associated with a camera, e.g., camera 56, to move the camera about the surgical site "S". For a detailed discussion of suitable foot pedals, reference may be made to U.S. Provisional Patent Application Ser. Nos. 62/510,502, filed May 24, 2017, entitled "PEDAL CONTROL FOR ROBOTIC SURGICAL SYSTEMS," (now International Patent Application Serial No. PCT/US2018/033084, filed on May 17, 2018), and 62/556,100, filed Sep. 8, 2017, entitled "HIGH PRECISION INSTRUMENT CONTROL MODE FOR ROBOTIC SURGICAL SYSTEMS," (now International Patent Application Serial No. PCT/US2018/049634, filed on Sep. 6, 2018). The entire contents of each of the above applications are hereby incorporated by reference.

Figure 2:
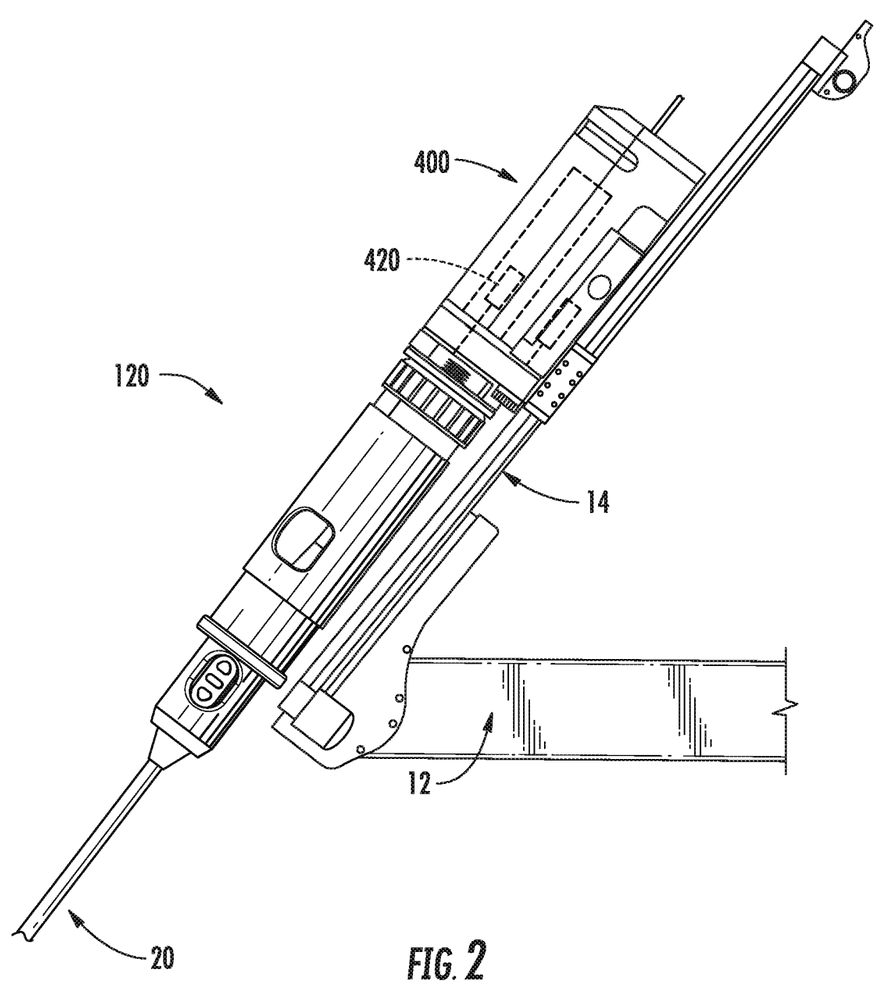
FIG. 2 is a side view of an end of an exemplary arm of a surgical robot of FIG. 1 including an IDU mounted to the arm.
Figure 3:
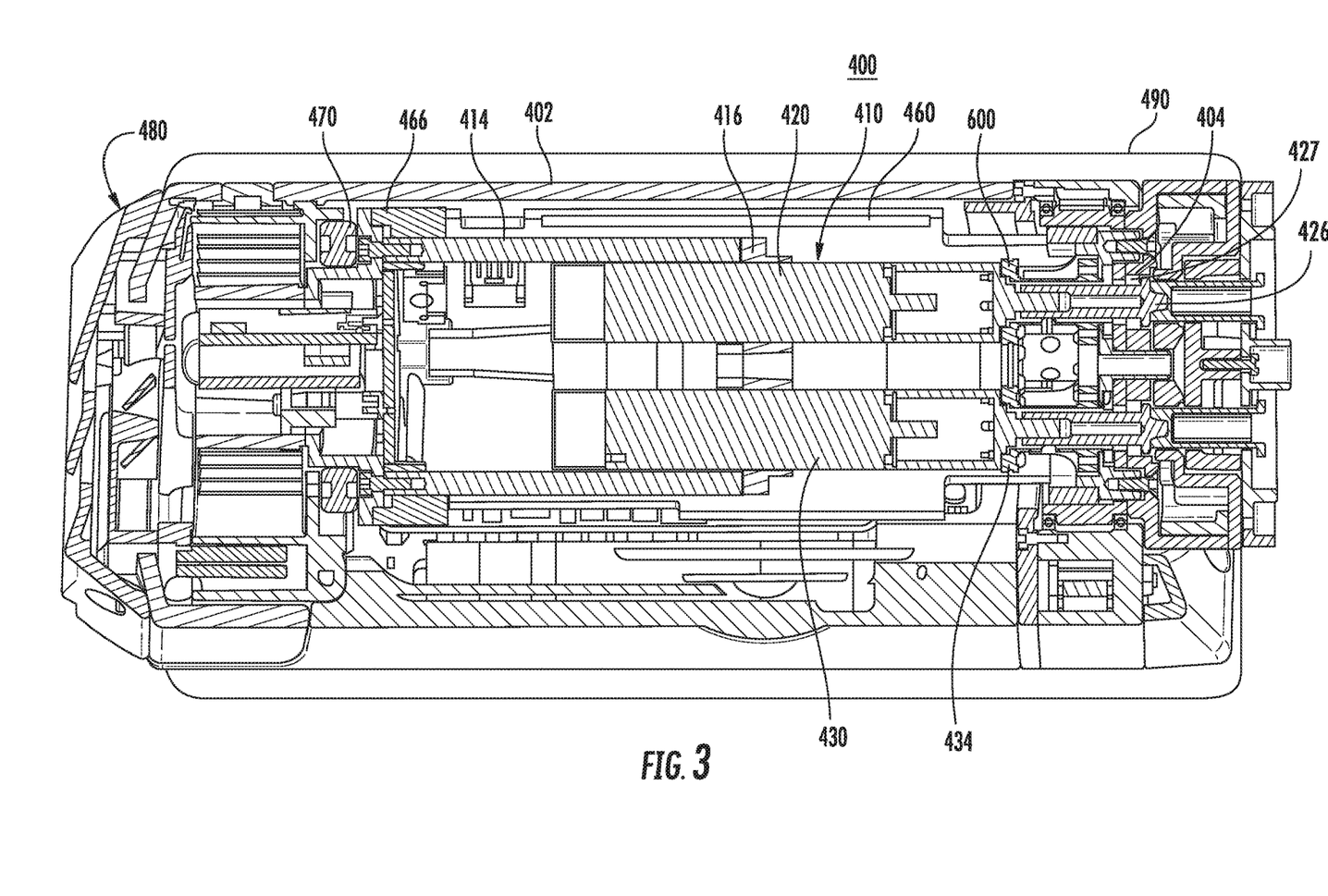
FIG. 3 is a longitudinal cross section of the IDU of FIG. 2.

With reference to FIGS. 2 and 3, the linkages 12 support an instrument drive unit 400 (IDU 400) on an end 14 thereof. The IDU 400 includes one or more motors 420 that cooperate to actuate an adapter assembly 120 to effect rotation of surgical instrument or tool 20. For a detailed discussion of suitable instrument drive units, reference may be made to U.S. patent application Ser. No. 15/887,391, filed Feb. 2, 2018 (now U.S. Pat. No. 10,213,266), the entire contents of which are hereby incorporated by reference.

With additional reference to FIG. 3, each of the motors 420 is mounted to a motor plate 404 within the IDU 400 by a torque transducer 600 that is configured to measure a torque $T_m$ of the respective motor 420 in real time. The motor plate 400 is configured to support each of the motors 420 relative to one another and in a known geometry with respect to one another. For example, the motor plate 400 may support four motors, e.g., motors 420, in a square pattern such that the four motors form a substantially rectangular brick shape with one another.

Figure 4:
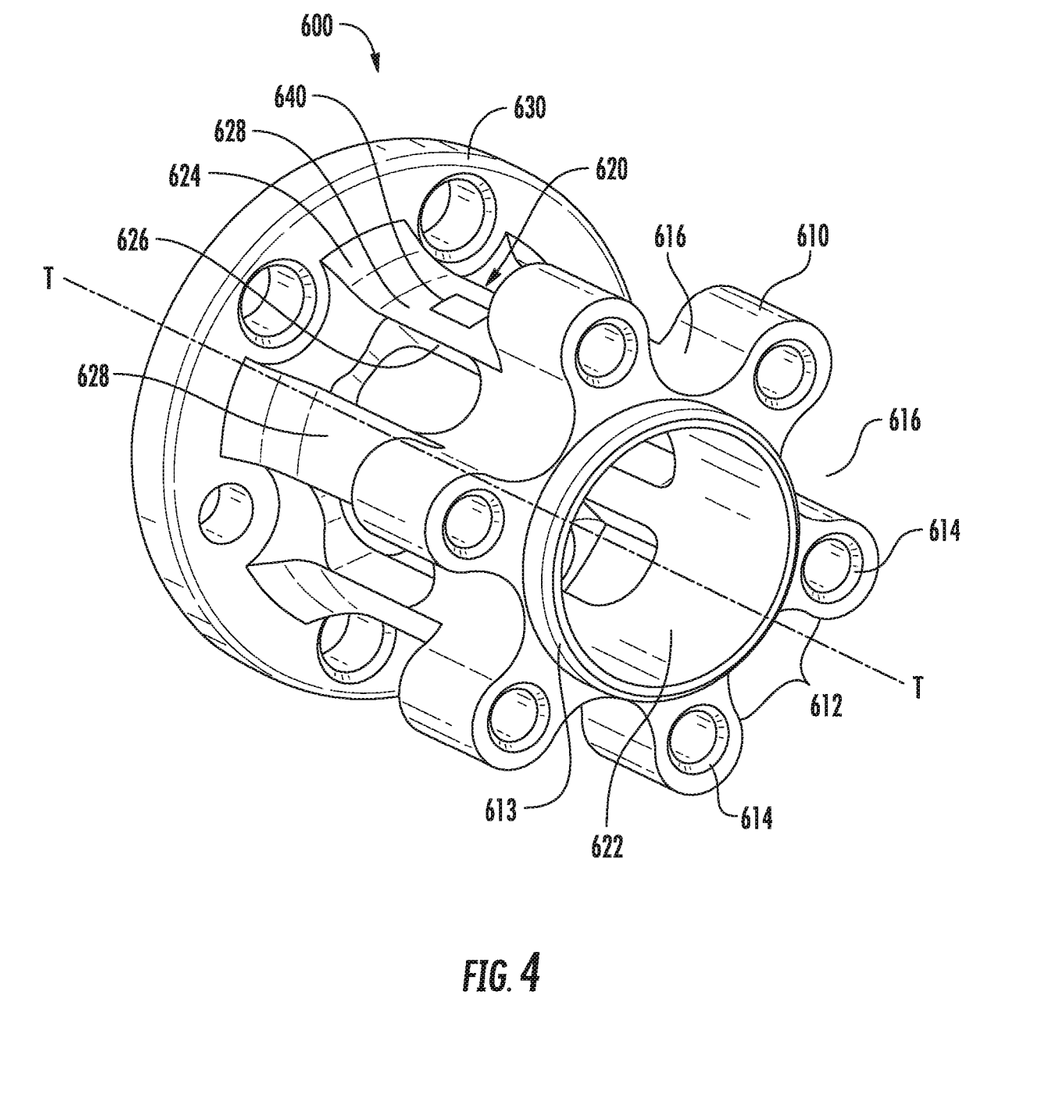
FIG. 4 is an exemplary torque transducer of the IDU of FIG. 3.

Referring to FIG. 4, the torque transducer 600 includes a mounting flange 610, a motor flange 630, and a body 620 interconnecting the mounting and motor flanges 610, 630. The mounting flange 610 is formed from a ring of radial protrusions 613 that each define a fastener hole 614 for receiving a fastener to secure the mounting flange 610 to a motor plate of the IDU 400, e.g., motor plate 404 (FIG. 3). The mounting flange 610 defines recesses 616 between each of the radial protrusions 613. The recesses 616 may be used to route wiring to a strain gauge 640 or between the IDU 400 and the adapter 120. Additionally or alternatively, the recesses 616 may provide driver access to the fasteners of the motor flange 630. The mounting flange 610 may include a locating feature or ring 612 that extends distally to position or locate the torque transducer 600 relative to the motor plate.

The body 620 is generally cylindrical and formed from a plurality of struts 628 that extend between the mounting and motor flanges 610, 630 to define a channel 622 through the body 620. The struts 628 are configured to deflect or flex in response to torque applied about the transducer axis T-T. The struts 628 include low stress regions 624 adjacent each of the mounting and motor flanges 610, 630 and a high stress region 626 between the low stress regions 624. The body 620 includes a strain gauge 640 disposed in the high stress region of at least one of the struts 628.

Figure 5:
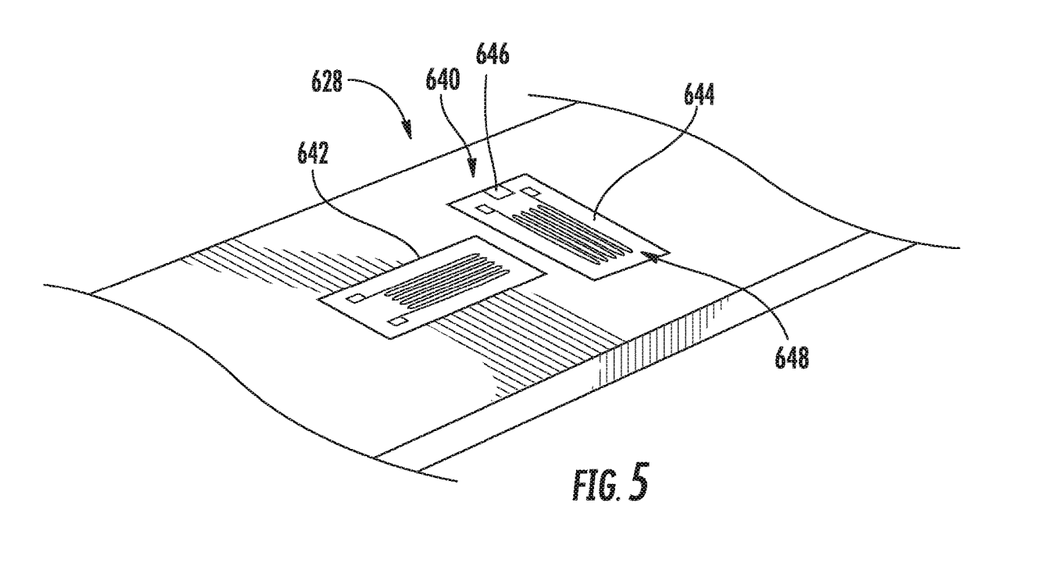
FIG. 5 is an enlarged partial view of a strut of the torque transducer of FIG. 4 including a strain gauge.

With additional reference to FIG. 5, the strain gauge 640 includes an active strain sensor 642 and a calibration strain sensor 644. The active strain sensor 642 is orientated to measure deflection or flex of the high stress region 626 in response to torque being applied to the torque transducer 600 about the transducer axis T-T (FIG. 4) as such the active strain sensor 642 measures radial strain of the high stress region 626. The calibration strain sensor 644 is aligned perpendicular to the active strain sensor 642 such that the calibration strain sensor 644 is subject to little or no radial deflection of the high stress region 626 about the transducer axis T-T. The calibration strain sensor 644 measures strain of the high stress region 626 in response to factors other than radial deflection, e.g., thermal expansion of the body 620. It is contemplated that the calibration strain sensor 644 can be used to detect axial tension or compressive forces. In addition, the calibration strain sensor 644 can be used to monitor for improper usage, linear drive thrust loads, and/or strain loading conditions of couplers. Further, the strain gauge 640 can include integrated electronics, e.g., EEPROM or microprocessors, to monitor life, gauge, cold starts, load limits, serialization, thermal limits, and calibration offsets that can be read and used to optimize and control the life of the strain gauge 640. The strain gauge 640 may be serialized and tracked during production and include a memory chip 646 (FIG. 4) which includes parameters of the strain gauge 640 including, but not limited to, a serial number and a measured gain particular to the strain gauge 640. In addition to the calibration strain sensor 644, each of the strain gauges 640 may include a temperature sensor 648. For a detailed discussion of torque transducers and strain gauges, reference may be made to U.S. Patent Publication No. 2016/0346049 (now U.S. Pat. No. 9,987,094) and U.S. patent application Ser. No. 15/887,391, filed Feb. 2, 2018 (now U.S. Pat. No. 10,213,266). The entire contents of each of the above disclosures are hereby incorporated by reference.

Figure 6:
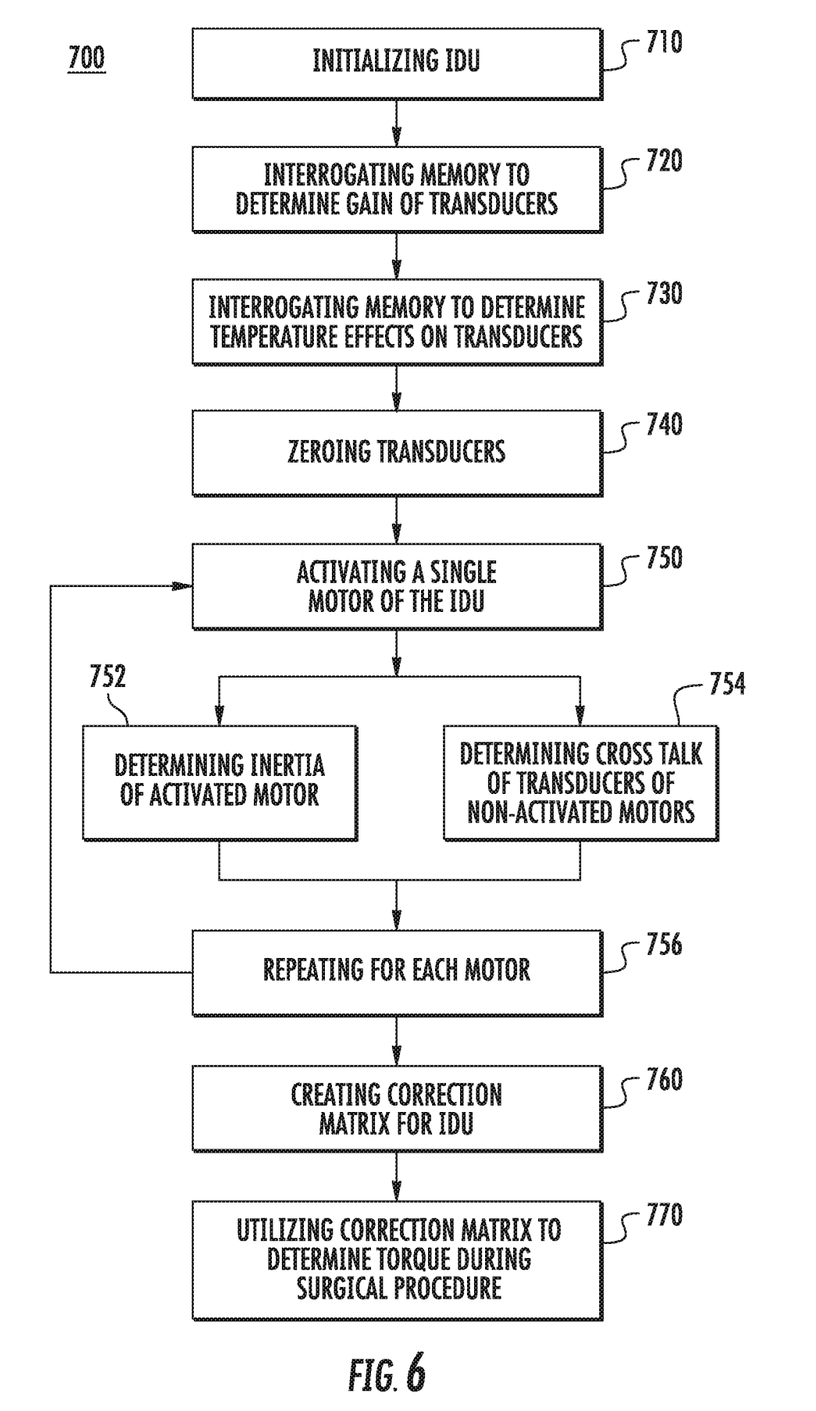
FIG. 6 is a flow chart of a method of calibrating torque transducers of an IDU for a surgical procedure in accordance with the present disclosure.

Referring to FIG. 6, a method 700 of calibrating and/or zeroing the torque readings of torque sensors is disclosed with reference to the processing unit 30, the IDU 400, motors 420, motor plate 404, torque transducers 600, and strain gauges 640 of FIGS. 1-4. It will be appreciated that while the method 700 is used to calibrate torque sensors of an IDU, the method 700 may be used to calibrate torque sensors of a variety of motors, e.g., a motor or motors of a hand held surgical instrument. Further, while the method 700 is described as being performed by processing unit 30, the entire method 700 or aspects of the method 700 may be executed by a controller disposed within the surgical robot 10 (FIG. 1) or within the IDU 400.

Initially, the processing unit 30 initializes the IDU 400 (Step 710) before the IDU 400 is coupled to a surgical instrument, e.g., surgical instrument 20. The processing unit 30 may interrogate the IDU 400 to receive a measured gain of each of the torque transducers 600 from a memory chip 646 of each of the torque transducers 600 (Step 720), or, optionally stored in a memory of IDU 400. The processing unit 30 may interrogate the IDU 400 to receive performance data of each of the torque transducers 600 relative to a temperature of the IDU 400 or a temperature of each of the torque transducers 600 (Step 730). The processing unit 30 may also interrogate, once, periodically, or continuously, a temperature of the IDU 400 or each of the torque transducers 600. It is contemplated that the IDU 400 may have a single memory chip that includes a gain for each of the torque transducers 600 of the IDU 400. The processing unit 30 also zeros each of the torque transducers 600 to set a zero load or zero torque $T_0$ for each of the torque transducers 600 (Step 740). For example, when each of the motors 420 is deactivated, the readings from each of the strain gauges 640 may be set to zero. During setting or zeroing of the torque transducers 600, the IDU 400 may be coupled to an adapter, e.g., adapter 120, with no load on any of the motors 420.

With each of the torque transducers 600 zeroed, the processing unit 30 determines an inertia J of each of the motors 420 and/or adapter 120 coupled to the IDU 400 (Step 752). To determine the inertia J associated with each of the motors 420, each of the motors 420 secured to the motor plate 404 are individually accelerated at a known, fixed rate with no load on the motors 420 and/or adapter 120 (Step 750). The known fixed rate can be verified by one or more position sensors (not explicitly shown) that measure the position of the motor 420. By accelerating the motor at a known, fixed rate, the inertia J of the respective motor 420, a gearbox, and/or adapter coupled to the IDU 400 can be determined. For example, when the respective motor 420 has an inertia J and is accelerated at a known angular acceleration a, the measured torque $T_m = J \cdot \alpha$. Thus, the inertia $J = T_m/\alpha$. With the inertia J known for each of the individual motors 420, the inertia J of each motor 420 can be compensated for by the processing unit 30 to increase the accuracy of control signals sent to the motors 420.

In addition, the processing unit 30 can determine a cross talk torque $T_c$ for each of the motors 420 when each of the motors 420 is individually accelerated at a known fixed rate (Step 754). Specifically, the cross talk torque $T_c$ of each of the other motors 420 is measured in response to the observed torque in the motor 420 being accelerated. The cross talk torques $T_c$ are then used to generate a 4×4 matrix, e.g., when the motor plate 404 has four motors 420 mounted thereto, to allow for correction of the cross talk torque $T_c$ for each of the motors 420 (Step 760). An exemplary cross talk matrix is shown in Table 1 below where the correction factors $C_xM_y$ is the $T_c$ measured at each motor Y when the motor X is being accelerated. For example, the $T_c$ of a first motor when a second motor is being accelerated is $C_2M_1$. The cross talk matrix of Table 1 is used to negate the effects of cross talk torque $T_c$ in each of the motors 420.

TABLE 1

$$\begin{bmatrix} 0 & C_2M_1 & C_3M_1 & C_4M_1 \\ C_1M_2 & 0 & C_3M_2 & C_4M_2 \\ C_1M_3 & C_2M_3 & 0 & C_4M_3 \\ C_1M_4 & C_2M_4 & C_3M_4 & 0 \end{bmatrix}$$

It will be appreciated that the processing unit 30 may more accurately control surgical instruments coupled to IDU 400 by compensating for an offset of each of the torque transducers 600 by zeroing the torque transducers 600, compensating for a gain of each of the torque transducers 600, compensating for a temperature of the IDU 400 and/or each of the torque transducers 600, an inertia of each of the motors 420, and/or a cross talk torque of each of the motors 420. More accurately controlling surgical instruments may allow for increased performance of a surgical robot during a surgical procedure which may improve surgical outcomes. In addition, the increased performance may reduce the amount of time required to complete a given surgical procedure which may decrease the cost of the surgical procedure.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A method of calibrating a torque sensor of a plurality of torque sensors, each of the torque sensors paired with a motor of a plurality of motors housed in an instrument drive unit (IDU), the method comprising:
    determining a gain of each torque sensor of the plurality of torque sensors, each torque sensor configured to measure torque of each motor of the plurality of motors;
    zeroing a torque reading of each of the torque sensors when each of the motors is in an unloaded, unactivated condition;
    accelerating each of the motors individually at a known rate in an unloaded condition while other motors in the IDU are in the unactivated condition; and
    determining an inertia of each of the motors in response to acceleration; and
    determining a cross talk torque of each of the torque sensors based on activation of each of the motors while other motors in the IDU are in the unactivated condition.

2. The method according to claim 1, wherein determining the gain of each of the torque sensors includes interrogating a memory chip of the torque sensor.

3. The method according to claim 1, wherein accelerating each of the motors individually at the known rate includes measuring a position of each of the motors with a corresponding position sensor of a plurality of position sensors.

4. A method of calibrating torque sensors of, each torque sensor associated with a respective motor of a plurality of motors housed in an instrument drive unit (IDU), the method comprising:

determining a gain of each of the torque sensors;
zeroing a torque reading of each of the torque sensors when each of the motors is in an unloaded, unactivated condition;
determining an inertia of each of the motors including:
   accelerating each of the motors at a known rate in an unloaded condition with each of the other motors in the IDU in an unloaded, unactivated condition;
   measuring a torque of the respective motor with a torque sensor associated with the respective motor; and
   determining the inertia of the respective motor from the measured torque and the known rate of acceleration; and
determining a cross talk torque of each of the torque sensors based on activation of each of the motors while other motors in the IDU are in the unactivated condition.

5. The method according to claim 4, wherein determining the gain of each of the torque sensors includes interrogating a memory chip of each of the torque sensors.

6. The method according to claim 4, wherein accelerating the respective motor at the known rate includes measuring a position of the respective motor with a position sensor associated with the respective motor.

7. The method according to claim 4, further comprising creating a cross talk matrix including a correction factor for each of the torque sensors for each of the motors of the IDU.

8. A method of calibrating torque sensors including a first torque sensor associated with a first motor, a second torque sensor associated with a second motor, a third torque sensor associated with a third motor, and a fourth torque sensor associated with a fourth motor, wherein the first, second, third, and fourth motors are housed in an instrument drive unit (IDU), the method comprising:
   determining a gain of each of the first, second, third, and fourth torque sensors;
   zeroing a torque reading of each of the first, second, third, and fourth torque sensors when each of the first, second, third, and fourth motors is in an unloaded, unactivated condition;
   determining an inertia of the first motor including:
      accelerating the first motor at a first known rate in an unloaded condition with each of the second, third, and fourth motors in an unloaded, unactivated condition;
      measuring a torque of the first motor with the first torque sensor; and
      determining the inertia of the first motor from the torque measured by the first torque sensor and the first known rate of acceleration;
   determining an inertia of the second motor including:
      accelerating the second motor at a second known rate in an unloaded condition with each of the first, third, and fourth motors in an unloaded, unactivated condition;
      measuring a torque of the second motor with the second torque sensor; and
      determining the inertia of the second motor from the torque measured by the second torque sensor and the second known rate of acceleration;
   determining an inertia of the third motor including:
      accelerating the third motor at a third known rate in an unloaded condition with each of the first, second, and fourth motors in an unloaded, unactivated condition;
      measuring a torque of the third motor with the third torque sensor;
      determining the inertia of the third motor from the torque measured by the third torque sensor and the third known rate of acceleration; and
   determining an inertia of the fourth motor including:
      accelerating the fourth motor at a fourth known rate in an unloaded condition with each of the first, second, and third motors in an unloaded, unactivated condition;
      measuring a torque of the fourth motor with the fourth torque sensor;
      determining the inertia of the fourth motor from the torque measured by the fourth torque sensor and the fourth known rate of acceleration; and
   determining a cross talk torque of each of the first, second, third, and fourth torque sensors based on activation of each of the first, second, third, and fourth motors while other motors are in the unactivated condition.

9. The method according to claim 8, wherein determining the inertia of the first motor includes determining a cross talk torque of the second, third, and fourth torque sensors in response to accelerating the first motor.

10. The method according claim 8, wherein determining the gain of the first, second, third, and fourth torque sensors includes interrogating a memory chip of each of the first, second, third, and fourth torque sensors.

11. The method according claim 8, wherein accelerating the first motor at the first known rate includes measuring a position of the first motor with a position sensor associated with the first motor.

12. The method according to claim 8, wherein determining the inertia of the second motor includes determining a cross talk torque of the first, third, and fourth torque sensors in response to accelerating the second motor; wherein determining the inertia of the third motor includes determining a cross talk torque of the first, second, and fourth torque sensors in response to accelerating the third motor; and wherein determining the inertia of the fourth motor includes determining a cross talk torque of the first, second, and third torque sensors in response to accelerating the fourth motor.

13. The method according to claim 12, further comprising creating a cross talk matrix including a correction factor for each of the first, second, third, and fourth torque sensors for torque from each of the first, second, third, and fourth motors.

14. The method according to claim 13, further comprising utilizing the cross talk matrix during a surgical procedure to correct torque of at least one of the first, second, third, or fourth motors.

* * * * *